United States Patent
Hess

Patent Number: 5,120,308
Date of Patent: Jun. 9, 1992

[54] CATHETER WITH HIGH TACTILE GUIDE WIRE

[75] Inventor: Robert Hess, Portola Valley, Calif.

[73] Assignee: Progressive Angioplasty Systems, Inc., Menlo Park, Calif.

[21] Appl. No.: 346,708

[22] Filed: May 3, 1989

[51] Int. Cl.[5] .......................... A61M 37/00
[52] U.S. Cl. ...................... 604/95; 604/96; 604/164; 128/657; 128/772
[58] Field of Search .......... 604/95, 96, 102, 164, 604/170, 280, 281, 282; 128/656, 657, 658, 772; 606/78

[56] References Cited

U.S. PATENT DOCUMENTS

| | | | |
|---|---|---|---|
| 3,868,956 | 3/1975 | Alfidi et al. | 606/78 |
| 4,411,655 | 10/1983 | Schreck | 604/281 |
| 4,427,000 | 1/1984 | Ueda | 128/6 |
| 4,543,090 | 9/1985 | McCoy | 604/95 |
| 4,601,283 | 7/1986 | Chikama | 128/4 |
| 4,601,705 | 7/1986 | McCoy | 604/95 |
| 4,608,986 | 9/1986 | Beranek et al. | 128/786 |
| 4,665,906 | 5/1987 | Jervis | 606/78 |
| 4,742,817 | 5/1988 | Kawashima et al. | 128/4 |
| 4,753,223 | 6/1988 | Bremer | 128/4 |
| 4,758,222 | 7/1988 | McCoy | 604/95 |
| 4,776,844 | 10/1988 | Ueda | 604/281 |
| 4,793,350 | 12/1988 | Mar et al. | 604/96 |
| 4,811,737 | 3/1989 | Rydell | 128/344 |
| 4,867,173 | 9/1989 | Leoni | 128/772 |
| 4,884,579 | 12/1989 | Engelson | 128/657 |
| 4,925,445 | 5/1990 | Sakamoto et al. | 604/281 |
| 4,926,866 | 5/1990 | Stice et al. | 604/281 |
| 4,934,380 | 6/1990 | de Toledo | 128/772 |
| 4,940,062 | 7/1990 | Hampton et al. | 128/772 |
| 4,984,581 | 1/1991 | Stice | 128/772 |

FOREIGN PATENT DOCUMENTS

| | | |
|---|---|---|
| 0141006 | 5/1985 | European Pat. Off. . |
| 0145489 | 6/1985 | European Pat. Off. ............ 128/772 |
| 0395098 | 10/1990 | European Pat. Off. . |

OTHER PUBLICATIONS

"Radifocus TM Guide Wire M" by Terumo Corporation, 1988.
"The Use of Pseudoelasticity in Guidewires and Arthroscopic Instrumentation" by Jim Stice, no date.
"Medical Applications and Fabrication Processes Using NiTi Alloys" by J. D. Stice, C. E. Sievert, Jr., S. J. Lind, G. F. Andreasen D.D.S., J. A. Vennes M.D., no date.

*Primary Examiner*—John D. Yasko
*Assistant Examiner*—Anthony Gutowski
*Attorney, Agent, or Firm*—Burns, Doane, Swecker & Mathis

[57] ABSTRACT

A catheter including an elongated highly flexible hollow lumen and a guide wire positioned within the lumen, the guide wire fabricated from nickel-titanium shape-memory alloy, the guide wire having greater than three percent (3%) elasticity over the temperature range of use of the catheter allowing high-elastic deformation at low stress and low rolling and sliding frictional resistance of the guide wire when moved and bent within the lumen producing a high degree of tactile control is disclosed.

15 Claims, 3 Drawing Sheets

CATHETER WITH HIGH TACTILE GUIDE WIRE

BACKGROUND OF THE INVENTION

1. Field of the Invention

The invention relates to guide wires and catheters commonly used in human arteries and specifically to improvements thereto incorporating shape-memory alloys.

2. Introduction to the Invention

Guide wires commonly used in human arteries (and particularly in coronary arteries) are commonly fabricated from type 304 stainless steel having a yield strength of about 300,000 psi and an elastic strain limit of about 1.375 percent. Such wires are easily used in relatively straight arteries, but the user experiences difficulties when such wires are used in more torturous arteries. Such wires are particularly difficult to use in torturous distal arteries in which the wire diameter would ideally be less than 0.018 inch. Such wires and catheters are usually, but not necessarily, introduced through the use of a guide catheter and are often slidably and rotationally mounted within a small lumen. This lumen is frequently fabricated from helically wound wire or a polymeric material.

As these devices are inserted into torturous arteries, the core wire is bent and forced against the wall of the inner lumen. Alternatively, if no inner lumen is used then the wire is bent and forced against the artery. In wires smaller than 0.018 inch in diameter, the yield strength of the wire would often be approached and could even be exceeded, resulting in plastic deformation (kinking) of the wire. Even when plastic deformation does not occur, considerable forces are exerted between the wire and the inner lumen or the artery. In this case it is necessary to overcome the static frictional forces to move the wire either slidably (to overcome sliding friction) or rotationally (to overcome rolling friction).

In the process of overcoming these frictional forces, considerable energy is stored in the wire prior to overcoming the frictional forces. Once the frictional forces are overcome, the energy is quickly released resulting in a "jerking" motion and the ensuing lack of control over the wire.

Although numerous coatings or coverings have been used in guide wire applications to lower the frictional coefficients with some degree of success, high forces still exist which tend to damage these coatings and cause plastic deformation of the wire. Stainless steel wires (with higher elastic limits) which have been highly work-hardened exert large stresses upon bending. Using such wires often presents difficulties when trying to maneuver them into branch arteries due to the amount of force (and resulting high stress) required to force a uniform radius into a branch. It would therefore be highly desirable to have a guide wire with the following properties: high-elastic deformation capability, low rolling and sliding frictional resistance, a small radius at low stress on bends, and tactile response.

In the past, shape-memory alloys have been used in medical applications due to the unique physical properties of the alloys U.S. Pat. No. 4,665,906, the disclosure of which is incorporated herein by reference, discloses the fact that materials possessing shape-memory are well-known and can be deformed from an original, heat-stable configuration to a second, heat-unstable configuration. These articles are said to have shape-memory for the reason that upon the application of heat alone, they can be caused to revert or attempt to revert from the heat-unstable configuration to the original, heat-stable configuration, i.e., because of the material, the article "remembers" its original shape.

The alloy possesses shape-memory because the alloy has undergone a reversible transformation from an austenitic metallurgical state to a martensitic metallurgical state upon changes in temperature. An article made from such an alloy is easily deformed from its original configuration to a new configuration when cooled below the temperature at which the alloy is transformed from the austenitic state to the martensitic state. The temperature at which this transformation begins is usually referred to as $M_s$, and the temperature at which it finishes is usually referred to as $M_f$. When an article thus deformed is warmed to a temperature at which the alloy starts to revert to austenite, referred to as $A_s$ ($A_f$ being the temperature at which the reversion is complete), the deformed article will begin to return to its original configuration.

Many shape-memory alloys are known to display stress-induced martensite when stressed at a temperature above $M_s$ (so that the austenitic state is initially stable), but below $M_d$ (the maximum temperature at which the martensite formation can occur even under stress) wherein an article made from the alloy first deforms elastically and then, at a critical stress, begins to transform by the formation of stress-induced martensite. If the temperature is below $A_s$, the stress-induced martensite is stable, but if the temperature is above $A_s$, the martensite is unstable and transforms back to austenite with the article returning (or attempting to return) to its original shape. The extent of the temperature range over which stress-induced martensite is seen, and the stress and strain ranges for the effect vary greatly with the alloy.

Many medical devices using shape-memory alloy rely upon the fact that when the shape-memory alloy element is cooled to its martensitic state and is subsequently deformed, it will retain its new shape, but when warmed to its austenitic state, the original shape will be recovered. U.S Pat. No. 4,665,906 introduces medical devices using shape-memory alloy which display stress-induced martensite rather than heat-recovery to perform a task, i.e., to do work in a medical device In these devices the shape-memory alloy component exhibiting stress-induced martensite is deformed into a deformed shape different from a final shape and is restrained by a separate restraining means, removal of the restraining means allowing the component and therefore the device to perform some operation. The disclosure of this patent is therefore limited to the concept of restraining the stored energy within the component of shape-memory alloy—it discloses, in essence, a spring. The disclosure is not suggestive of a medical device capable of high-elastic deformation, exhibiting low rolling and sliding frictional resistance, and which provides a tactile response.

U S. Pat. No. 4,776,844 discloses a medical tube having an elastic member embedded in the peripheral wall of the tube for keeping the tube straight wherein the elastic member is formed of a high-elastic alloy (a shape-memory alloy). The transformation temperature at which the alloy transforms in phase from the martensite structure to the austenite structure is set at a temperature lower than the temperature at which the medical tube is used. The "high-elastic alloy" is a shape-memory alloy believed to be displaying stress-induced martensite wherein one or more elastic members are embedded in the device—again acting like a spring to prevent the device from buckling. The embedded shape-memory alloy components, as discussed with reference to FIGS. 10-12 of the patent, may also display heat-recovery when the driving member 42 is heated by warm water to again perform work. None of the embodiments suggests a guide wire of shape-memory alloy alone wherein the guide wire is capable of high-elastic deformation and has low frictional resistance which allows tactile control of such a wire when passed alone through an artery or when slidably mounted within a small diameter lumen of a catheter.

A recent (but believed to be unpublished) paper entitled "Medical Applications and Fabrication Processes Using NiTi Alloys" written by Stice, Sievert, Jr., Lind, Andreasen and Vennes discloses many uses of shape-memory alloys. In the section entitled "Orthopedics-Arthroscopic Instrumentation" a curved cannula with an initially straight shape-memory alloy needle is disclosed. The shape-memory alloy component bends due to the property of nickel-titanium called "pseudo-elasticity" which is a term commonly used instead of "stress-induced martensite". This disclosure is the opposite of that described in U.S. Pat. No. 4,665,906 wherein the alloy component was bent and was restrained to a straight position by another member. The disclosure of the paper does not suggest the guiding of the device with a guide wire capable of high-elastic deformation and low frictional resistance necessary for tactile response.

The paper discusses the substitution of shape-memory alloy for stainless steel in a guide wire to at least partially eliminate the use of a helically wound coil recovery member which supports a stainless steel guide wire. Trauma is thought to be caused by the coils. Regardless of whether or not the paper can be considered to be prior art, it does not disclose or suggest the application of shape-memory alloy in small diameter wires, i.e., less than 0.018 inch, where full coil wires are not conventionally used but where the stiff core of wire itself pressing against the wall of an artery at a bend will cause trauma. This trauma is more severe in the case where a full coil envelopes the stainless steel core in large diameter cores but is still caused fundamentally by the stiffness of the stainless steel core wire in small diameter cores not suggested by the paper. It would therefore be desirable to have a guide wire of small diameter which is capable of being bent at low stress levels with high-elasticity such that when inserted into tortuous arterial passages, the forces exerted on the artery walls are low, thereby minimizing trauma to the artery.

The brochure entitled "Radifocus ™ Guide Wire M" by Terumo disclosed the use of a super-elastic "core material" imbedded in a hydrophilic polymer. In this application the wire forms the core of a composite construction with a thick polymer outer layer which extends beyond the distal end of the core wire. The wire has no provision for a platinum floppy tip. The polymer and the lack of a floppy tip eliminate the possibility of shaping the tip to enhance steerability. The absence of a heavy metal at the distal end also makes it difficult or impossible to see in a human artery under fluoroscopy; steering the wire to a particular branch or lesion is not possible since the wire cannot be seen. The relatively large diameter Terumo wire is therefore similar in structure and function to the device described earlier in U.S. Pat. No. 4,776,844 where the shape-memory alloy is embedded in the device and acts like a spring to prevent the device from buckling.

SUMMARY OF THE INVENTION

The purpose of the invention is to provide a guide wire and catheter for use in human arteries (and particularly coronary arteries) wherein the guide wire is capable of high-elastic deformation, has low rolling and sliding frictional resistance and a high degree of straightness wherein the wire in use will guide the catheter through the arteries thus providing the operator with a tactile response. To accomplish this purpose there is provided a guide wire (or a combination of lumen and guide wire comprising a catheter) wherein the guide wire has greater than three percent (3%) elasticity, the guide wire offering low rolling and sliding frictional resistance within the artery or lumen, the guide wire being unstressed prior to bending, and being confined to a small radius at low overall stress in tortuous arteries or at branches.

In one aspect of the invention there is provided a catheter comprising: a lumen, said lumen being an elongated, highly flexible hollow member; and a guide wire positioned within said lumen, said guide wire fabricated from nickel-titanium shape-memory alloy, the guide wire having greater than three percent (3%) elasticity at a stress level of at least about 60,000 psi over the temperature range of use of the guide wire allowing high-elastic deformation at low stress and low rolling and sliding frictional resistance of the guide wire when moved and bent within said lumen, said guide wire being generally circular in cross-section having a diameter less than 0.018 inch to accommodate a minimum diameter lumen for use in distal coronary arteries, said guide wire being initially straight and having no stored energy within the guide wire prior to movement and bending of the guide wire, said guide wire being in a metallurgical state wherein the guide wire moves freely within said lumen through small radius bends without buckling or kinking, thereby producing a high degree of tactile control.

In another aspect there is provided a guide wire fabricated from nickel-titanium shape-memory alloy, the guide wire having greater than three percent (3%) elasticity at a stress level of at least about 60,000 psi over the temperature range of use of the guide wire allowing high-elastic deformation at low stress and low rolling frictional and sliding resistance of said guide wire when moved and bent, said guide wire having a diameter less than 0.018 inch, said guide wire being initially straight and having no stored energy within said guide wire prior to movement and bending of said guide wire, said guide wire being in a metallurgical state wherein said guide wire bends through small radius bends without buckling or kinking, thereby producing a high degree of tactile control.

In yet another aspect of the invention there is provided a guide wire comprising: an elongated hollow body portion having a proximate end and a distal end; an extension wire fabricated from nickel-titanium shape-memory alloy, the extension wire having greater than three percent (3%) elasticity at a stress level of at least about 60,000 psi over the temperature range of use of the guide wire allowing high-elastic deformation and low frictional and sliding resistance of said extension wire when moved and bent, said extension wire being initially straight and having no stored energy within said extension wire prior to movement and bending of said extension wire, said extension wire having a series of tapered sections providing variable strength along the length thereof from greater to lesser strength extending away from the distal end of said hollow body portion to provide trackability, pushability and flexibility of said guide wire; a flexible wire fixed to and extending axially away from said extension wire, said flexible wire comprising a floppy tip for said guide wire; an inflatable balloon connected to said body portion and extending over the length of said extension wire; and means to inflate said balloon.

Still in another aspect of the invention there is provided a guide wire fabricated from nickel-titanium shape-memory alloy wherein said guide wire has a low friction, high strength coating of polyimide polymer, said coating cured at a temperature which does not detrimentally affect the straightness and strength of the shape-memory alloy.

DESCRIPTION OF THE PREFERRED EMBODIMENTS

Figures 1, 2, 3, 4:
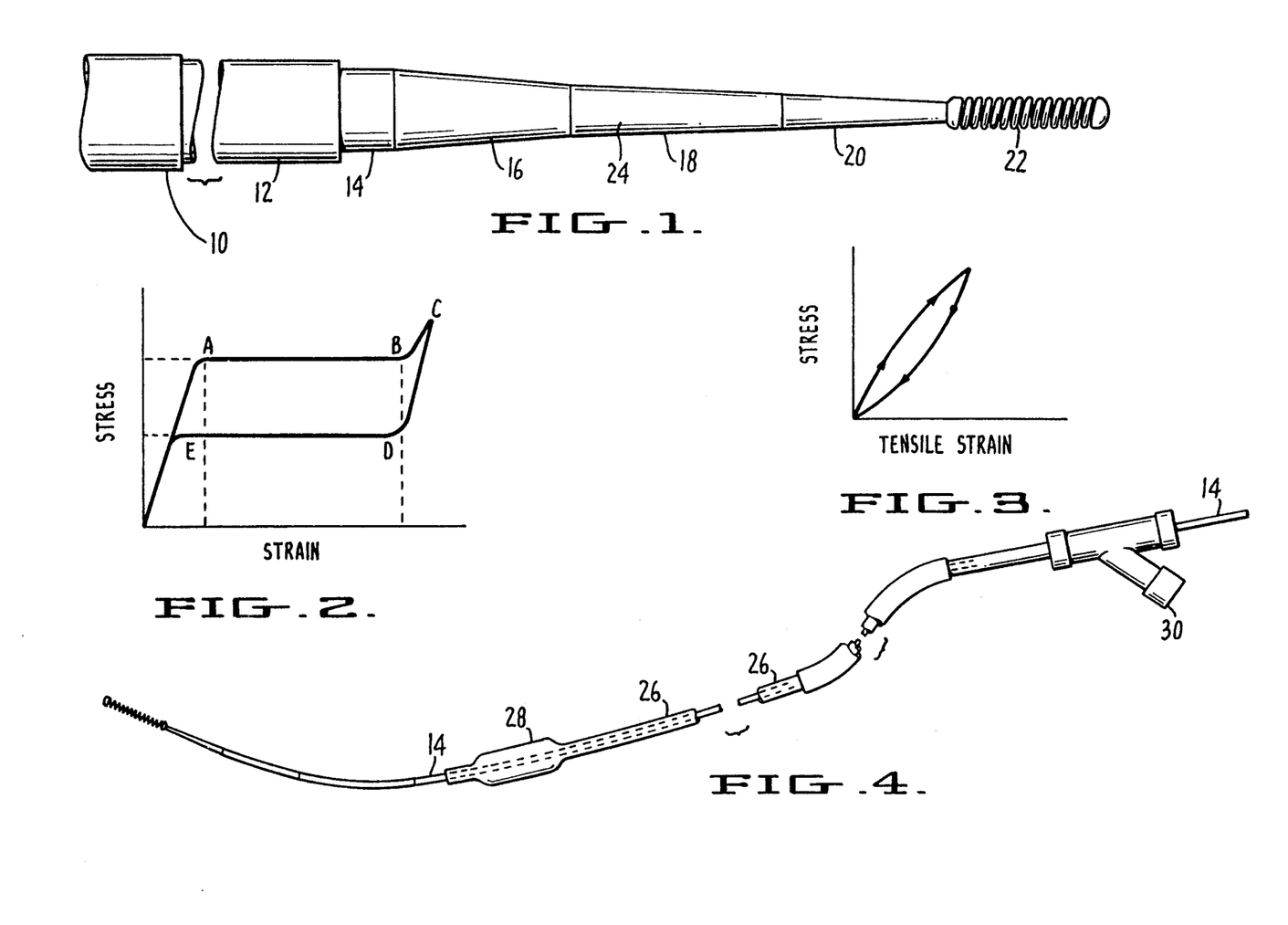
FIG. 1 is a partial perspective view of the distal end of a guide wire and lumen using the guide wire of the invention and a guide catheter.
FIG. 2 is a stress-strain diagram of a shape-memory alloy used to fabricate a guide wire of the invention wherein the alloy exhibits stress-induced martensite (pseudo-elasticity)
FIG. 3 is a stress-strain diagram similar to FIG. 2 of a shape-memory alloy used to fabricate a guide wire of the invention wherein the alloy exhibits super-elasticity.
FIG. 4 is a partial perspective view of an alternate embodiment of the catheter partially shown in FIG. 1 including an inflatable balloon over one end of the lumen of the catheter including means to inflate the balloon.

With continued reference to the drawing, FIG. 1 illustrates a catheter 10 including a lumen 12 and a guide wire 14 in accordance with the invention. The lumen 12 is an elongated, highly flexible hollow member. The lumen 12 is preferably fabricated from a helically wound wire which is preferably coated on the outside and/or the inside for various purposes including the facilitation of the transmission of fluids therethrough.

Guide wire 14 is positioned within the lumen 12 and is fabricated from a nickel-titanium shape-memory alloy having greater than three percent (3%) elasticity which allows the guide wire 14 high-elastic deformation at low stress. Such a guide wire may have as much as an order of magnitude more elasticity at low stress than conventionally known stainless steel wires. In coronary arteries, particularly distal arteries, the high elastic deformation of the guide wire enables the guide wire to maneuver through "small radius bends", e.g., less than three-fourths ($\frac{3}{4}$) of an inch. In such distal arteries the diameter of the guide wire of the instant invention would ideally be less than 0.018 inch.

Again, the guide wire 14 of the invention has greater than about three percent (3%) elasticity which, in the very small diameter desired for use in distal arteries, allows the guide wire to experience multiple bends while being moved through the artery (or through a lumen moved through the artery) yet still be capable of linear and rotational movement within the artery and/or lumen without the guide wire approaching its yield strength. (Conventional stainless steel wire would approach its yield strength, resulting in plastic deformation or "kinking" of the wire.)

The selection of a shape-memory alloy and its metallurgical state during use allows a high degree of elasticity which is a key aspect of the invention in that it allows one to take a very small diameter guide wire which will undergo a high degree of bending when the guide wire is forced against the wall of either a lumen or the wall of a distal artery without impeding movement of the wire. FIGS. 2 and 3 illustrate stress-strain diagrams of suitable alloys which exhibit the high-elasticity necessary in the subject invention. It is believed that altering the properties of the guide wire by using the particular shape-memory alloy provides the unexpected result of greater elastic deformation at much lower loads. This effect is localized at bends where martensite is being stress induced.

The fact that the wire can be bent at much lower loads and that as bending proceeds, or is forced to proceed, the additional stress required is low allows changes in direction within the arteries with much greater ease. This may also allow access to arterial branches that have heretofore been impossible or difficult to reach.

Figure 9:
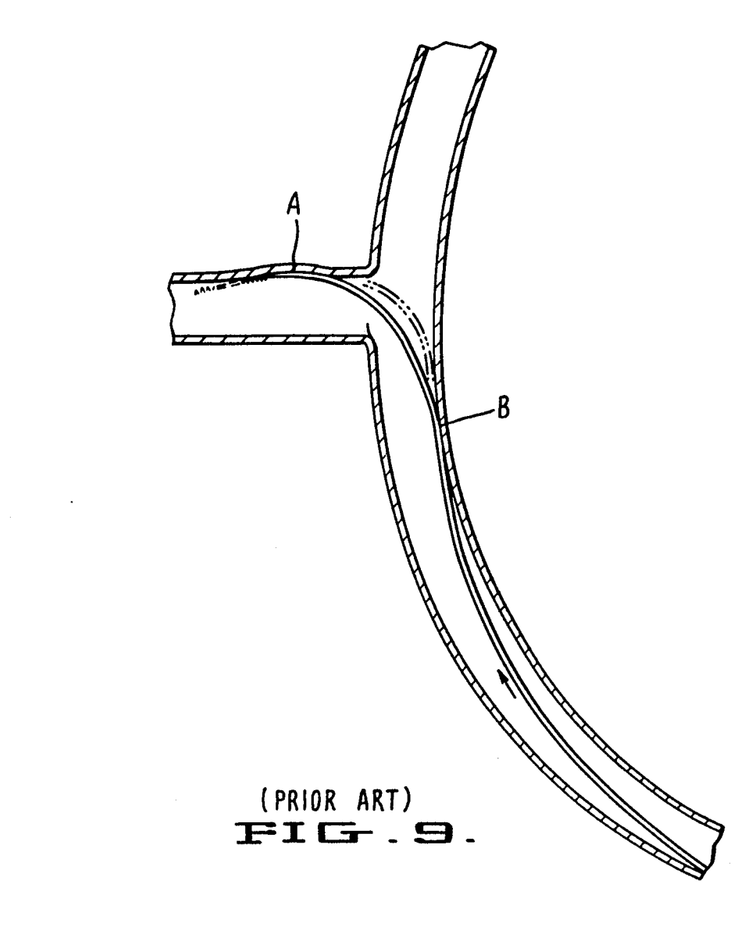
FIG. 9 is a cross-sectional view of an artery illustrating the advancement sequence of a typical stainless steel guide wire with the initial position of the wire shown in solid line and subsequent position shown in phantom.

A typical stainless steel wire has a Young's Modulus (E) of about $35 \times 10^6$ psi. Since deflection (f) in such material varies directly with the stress (S) and inversely as the Young's Modulus, we get f varies as $_E^S$ so that a greater deflection requires a proportionally greater stress. Deflection occurs uniformly with constant radius in such materials, and as the stress is increased to force a bend (change in direction) the wire may be pulled out of the branch artery. Due to the high stress at points A and B, as shown in FIG. 9, and required contact with the artery wall, considerable trauma to the artery wall can result.

Figure 10:
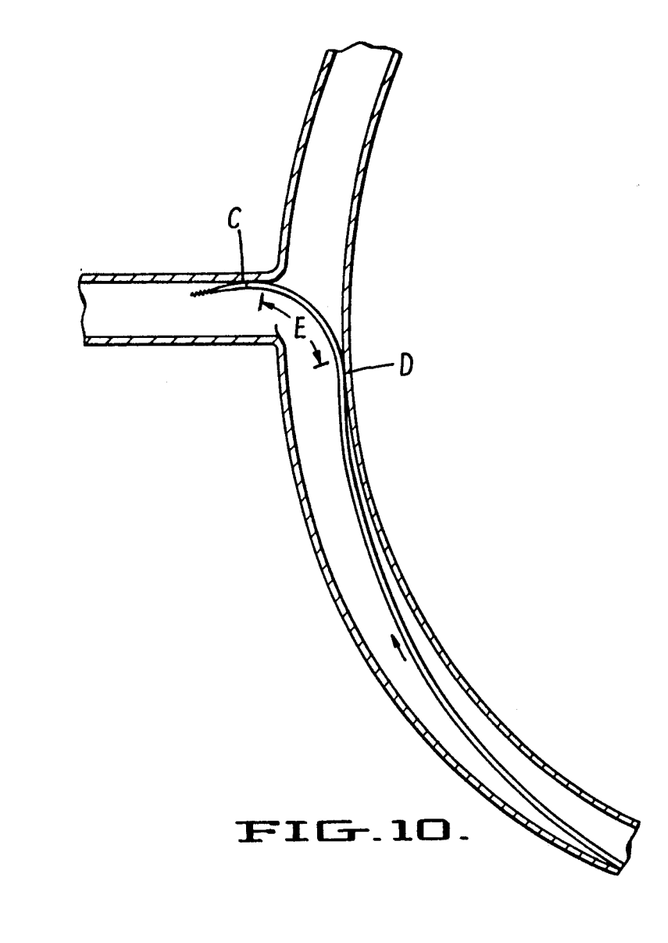
FIG. 10 is a cross-sectional view similar to FIG. 9 illustrating the advancement of a shape-memory alloy wherein the alloy exhibits stress-induced martensite.

In the nickel-titanium alloys of the present invention f varies as $_E^S$ does not apply once bending has been initiated, as can be seen in FIG. 2. Once bending is initiated, very little additional stress is required to continue the bend. Also, since the mechanism is stress-induced martensite which occurs only "locally" in the region stressed, a non-uniform deflection can occur without the requirement of a uniform radius. In fact, the material is not homogenous in that region shown as E in FIG. 10. This allows high local bending of the guide wire 14, thus permitting sharp changes in direction at low stresses, as shown in FIG. 10, at points C and D, and greatly reducing the tendency for a wire to be pulled out of a branch artery while attempting to advance into that artery and the trauma resulting from high stresses. The above discussion is believed to explain the interrelationship of what is defined as "high-elastic deformation at low stress" accomplished by use of shape-memory alloys having "greater than zero elasticity", the guide wire so defined "moving freely" through "small radius bends" without "buckling or kinking", thereby minimizing trauma to the artery walls. These structural limitations, and particularly the low stress level as compared to stainless steel, distinguish the present invention from the mere substitution of shape-memory alloy for coils to prevent buckling (thereby reducing trauma) as suggested in the Stice et al. paper.

FIG. 2 illustrates the phenomenon of stress-induced martensite by means of a stress-strain curve. It is understood that the phenomenon of pseudo-elasticity is synonymous with the concept of stress-induced martensite.

FIG. 3 illustrates, by means of a stress-strain curve, the phenomenon of super-elasticity The use of either a pseudo-elastic material or a super-elastic material significantly reduces the load on the wire in either an artery or a lumen as part of a catheter. For example, a pseudo-elastic shape-memory alloy of nickel-titanium could have a stress-induced martensite of about 60,000-100,000 psi and an elastic range of three percent (3%) or more at that stress level. It is understood that a super-elastic material of nickel-titanium having similar stress-strain characteristics of stress-induced martensite of at least about 60,000 psi and an elastic range of three percent (3%) or more at that stress level can be used. A guide wire 14 fabricated from such a material would exert about one-third (⅓) the load as a type 304 stainless steel wire within the inner lumen. For example, in the calculation of rolling friction:

$$P = r^k L$$

where
P is equal to the resistance in rolling
k is equal to a friction constant
r is equal to the radius of the rolling body, and
L is equal to the load on the rolling body.

Clearly, the resistance to rotational motion is directly proportional to the load, and the load in the case of a nickel-titanium wire according to the invention for high strain values is greatly reduced. A similar analysis can be made for the case of sliding friction:

$$F = fN$$

where
F is equal to the force resisting sliding
f is equal to the friction coefficient, and
N is equal to the load.
Again, since the load is reduced to about one-third (⅓), the resistance to motion is greatly reduced.

Figure 7:
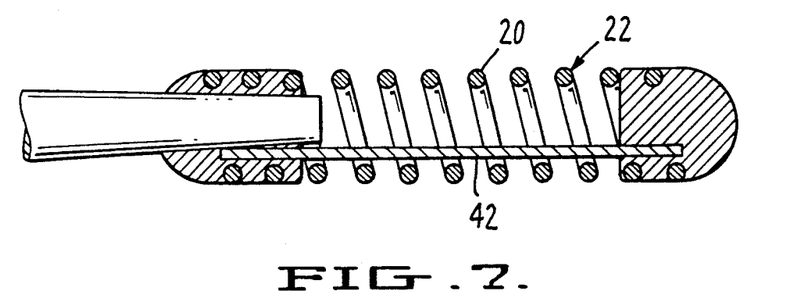
FIG. 7 is a cross-sectional enlargement of the distal end of the guide wire shown in FIGS. 1, 4 and 5 showing a flexible wire fixed and axially extending away from the far end of the guide wire wherein the flexible wire comprises a floppy tip for the guide wire and further including an additional safety wire interconnecting the guide wire and flexible wire.

FIG. 1 shows the detailed structure of the guide wire 14 wherein the guide wire is non-uniform in cross-section. Specifically, guide wire 14 preferably comprises a plurality of tapered sections 16, 18 and 20. Although three sections are shown, it is understood that any number of sections and/or a continuous taper are within the scope of the invention. A flexible wire 22 is fixed to and axially extends away from the far or distal end of the guide wire 14. The flexible wire 22 comprises a floppy tip for the guide wire 14. FIG. 7 illustrates the floppy tip construction which will be discussed later.

Guide wire 14 may optionally be completely or partially coated, as noted at 24, to lower the overall frictional coefficient of the guide wire. Such coatings could include polytetrafluroethylene (TFE) and silicones such as Dow Corning type MDX. Such materials have been used to lower the frictional coefficients of conventional guide wires, but high forces still exist which tend to damage these coatings The high application temperature associated with TFE makes it difficult to apply to nickel-titanium alloys of this type while maintaining straightness and strength of the guide wire. It is important that the thickness of the coating be relatively thin compared to the diameter of the guide wire so as not to alter the performance of the guide wire.

Certain polyimide polymers are preferred as a coating since they are capable of being applied in thin, strong, damage-resistant films at temperatures which do not alter the properties of the nickel-titanium alloy. The polyimide polymers possess coefficients of friction which are nearly as low as TFE. Although polyimide polymers are well-known for their electrical and strength properties, they are not known to be used (especially in medical products) for their low coefficient of friction The preferred polyimide polymers are those which cure at temperatures which are not detrimental to the properties of the nickel-titanium alloys. A preferred polyimide is available from the Electronic Materials Division of the DuPont Company under the description Pyralin ®PI-2550. It is within the scope of this aspect of the invention to use such polyimide polymers on conventional stainless steel guide wires In the case of a guide wire having a diameter less than 0.018 inch, the coating should not exceed 0.0015 inch in thickness and preferably should not be more than 0.0005 inch in thickness. The use of the shape-memory alloy wire reduces these forces, and the performance of the wire and the coating can therefore be enhanced by using the friction-reducing coating.

FIG. 4 shows an alternate embodiment of the catheter wherein the lumen 26 further includes an inflatable balloon 28 over the far end of the lumen 26 and further includes means 30 to inflate the balloon so that the catheter can be used in an angioplasty procedure. A guide wire 14, like that described with respect to FIG. 1, is slidably mounted within the lumen 26. The guide wire 14 is advanced through the lumen 26 to negotiate through the artery. The catheter (containing the trough lumen) can then be advanced along the wire. When the catheter is advanced to the site of a lesion the balloon is placed across the lesion and inflated, thus dilating the lesion.

Figure 5:
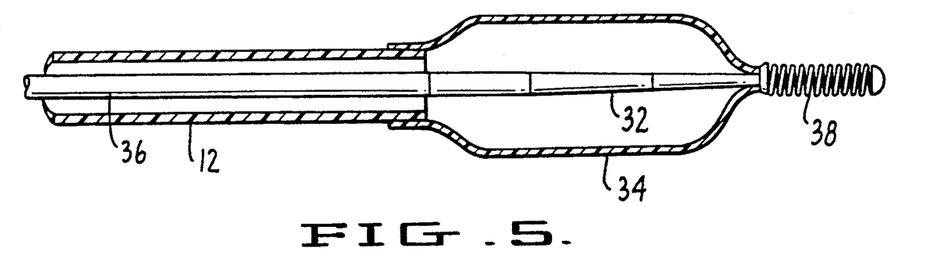
FIG. 5 is a partial cross-sectional view of yet another embodiment including an inflatable balloon over one end of the guide wire of the catheter.

FIG. 5 shows another alternate embodiment of the invention. Guide wire 32 is similar to the guide wire shown in FIGS. 1 and 4 but further includes an inflatable balloon 34 and means 36 to inflate the balloon. Inflatable balloon 34 is mounted toward the end of the guide wire 32, the floppy tip 38 extending beyond the balloon to assist in steering the guide wire. In this embodiment the guide wire 32 replaces the guide wire 14 and the lumen 12 of FIG. 1 (this is not an "over the wire" device) and allows a very low profile. This catheter will be harder to maneuver because it is not "over the wire"; therefore, the advantages of steering associated with shape-memory alloy are even more important.

Figure 6:
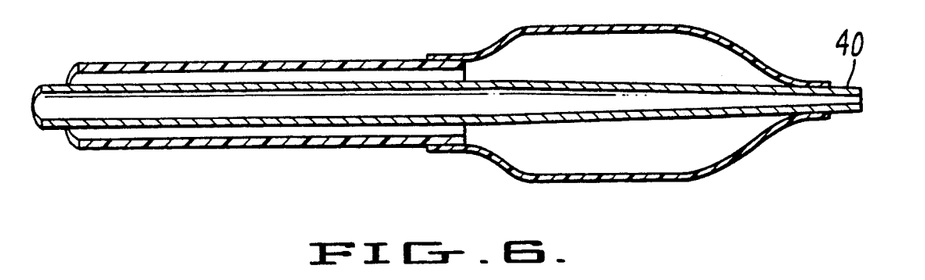
FIG. 6 is a partial cross-sectional view of an alternate embodiment of the guide wire in a catheter wherein the guide wire is hollow and further including an optional inflatable balloon over one end of the hollow guide wire.

FIG. 6 illustrates an alternate embodiment of the catheter and guide wire wherein the guide wire 40 is hollow. In this case the guide wire can become a lumen with 0.012 inch to 0.020 inch outside diameter and 0.008 inch to 0.016 inch inside diameter. Another wire (not shown) may then be inserted through the lumen and a balloon placed on the lumen. In the alternative, the lumen can be sealed at the distal end and a balloon also placed on the lumen.

It is understood with respect to all of the embodiments described above that the guide wire from each embodiment is useful with or without a lumen. Specifically, a guide wire fabricated from nickel-titanium shape-memory alloy wherein the guide wire has greater than three percent (3%) elasticity and which allows high-elastic deformation and low frictional sliding resistance of the guide wire has advantages over guide wires previously known or used in catheters or directly in the arteries. It is understood that such a guide wire is initially straight and has no stored energy within the guide wire prior to movement and bending of the guide wire.

FIG. 7 is an enlarged view of the end of the guide wire 14, shown in FIGS. 1 and 4 as well as that shown in FIG. 5, without a balloon Flexible wire 22 is fixed to and axially extends away from the end of the guide wire 14, specifically the last tapered section 20 of the guide wire The flexible wire 22 comprises a floppy tip for steering the guide wire. An additional safety wire 42 interconnects the guide wire 14 and the flexible wire 22 and allows shaping of the flexible wire 22 to aid in steering of the wire. The flexible wire 22 of the floppy tip is generally fabricated from gold, platinum or other heavy metal to provide radiopacity so the wire can be visualized under x-ray. The flexible wire 22 is connected to the guide wire in the area of the gold-plating by low temperature methods. High temperature methods related to welding can adversely affect shape-memory alloy material properties. Safety wire 42 is generally fabricated from type 304 stainless steel.

Figure 8:
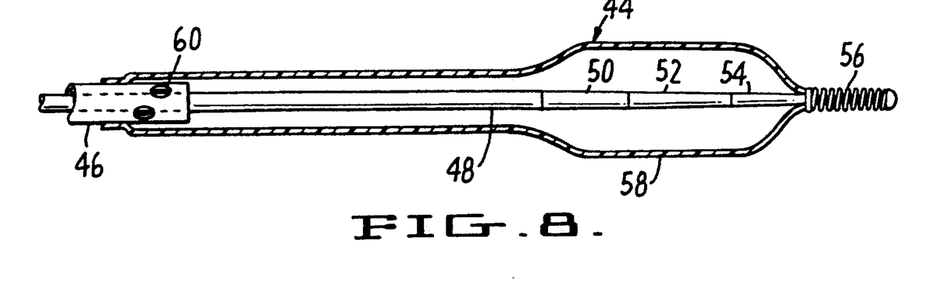
FIG. 8 is a partial cross-sectional view similar to FIG. 1 of yet another embodiment of the catheter including an inflatable balloon over the lumen portion of the catheter and the guide wire.

FIG. 8 shows yet another embodiment of the invention wherein a guide wire, shown generally at 44, includes a hollow body portion similar to that shown in FIG. 6. Body portion 46 may be made from shape-memory alloy or from a conventional material such as stainless steel. An extension wire 48 fabricated from nickel-titanium shape-memory alloy (the extension wire having greater than three percent [3%] elasticity over the temperature range of use of the guide wire allowing high-elastic deformation and low frictional and sliding resistance of the extension wire when moved and bent) is attached to the end of body portion 46. Similar to the embodiments discussed earlier, the extension wire 48 is initially straight and has no stored energy within the extension wire prior to movement and bending of the extension wire. The high flexibility of the extension wire, which preferably has a plurality of tapered sections 50, 52 and 54, provides variable strength along the length thereof from greater to lesser strength extending away from the distal end of the hollow body portion 46 to provide trackability, pushability and flexibility of the guide wire. A flexible wire 56 is fixed to and extends axially away from the extension wire 48. Guide wire 44 also includes an inflatable balloon 58 which is connected to the body portion 46 and extends over the length of the extension wire 48. Means 60 to inflate the balloon 58 is also included It will be obvious to those skilled in the art having regard to this disclosure that other variations on this invention beyond those specifically exemplified here may be made. Such variations are, however, to be considered as coming within the scope of the invention and are limited solely by the following claims.

What is claimed is:

1. A catheter comprising:
   a lumen, said lumen being an elongated, highly flexible hollow member; and
   a guide wire positioned within said lumen, said guide wire having a far end and being fabricated from nickel-titanium shape-memory alloy, said guide wire being of substantially straight configuration along its length including said far end and having greater than three percent (3%) elasticity at a stress level of about 60,000 psi over the temperature range of use of said guide wire allowing high-elastic deformation at low stress and low rolling and sliding frictional resistance of said guide wire when moved and bent within said lumen due to said elasticity at said stress level, said guide wire being generally circular in cross-section having a diameter less than 0.018 inch to accommodate a minimum diameter lumen for use in distal coronary arteries, said guide wire being initially straight and having no stored energy within said guide wire prior to movement and bending of said guide wire, said guide wire being in a metallurgical state wherein said guide wire moves freely within said lumen through small radius bends without buckling or kinking, thereby producing a high degree of tactile control, said guide wire having a low friction coating bonded thereto, said coating cured at a low temperature that is not detrimental to the straightness and strength of the nickel-titanium shape-memory alloy, said coating being less than 0.0015 inch in thickness to minimize the overall diameter of the guide wire, said coating generally extending along the length of said guide wire, said guide wire including a flexible wire fixed to and extending away from said far end of said guide wire beyond said coating, said uncoated flexible wire comprising a floppy tip for said guide wire.

2. A catheter as in claim 1 wherein said lumen is fabricated from helically wound wire 3. A catheter as in claim 1 wherein said shape-memory alloy is pseudo-elastic displaying reversible stress-induced martensite.

4. A catheter as in claim 1 wherein said shape-memory alloy is super-elastic.

5. A catheter as in claim 1 wherein at least a portion of said guide wire is non-uniform in cross-section exhibiting a stress-induced variable modulus at a point of bending along said portion due to high stress.

6. A catheter as in claim 1 further including an inflatable balloon over one end of said lumen and further including means to inflate said balloon.

7. A catheter as in claim 1 further including an inflatable balloon over one end of said guide wire and further including means to inflate said balloon.

8. A catheter as in claim 1 wherein said flexible wire is helically wound and further including an additional safety wire interconnecting said guide wire and said flexible wire.

9. A guide wire having a far end and being fabricated from nickel-titanium shape-memory alloy, said guide wire having greater than three percent (3%) elasticity at a stress level of about 60,000 psi over the temperature range of use of said guide wire allowing high-elastic deformation at low stress and low rolling and sliding frictional resistance of said guide wire when moved and bent due to said elasticity at said stress level, said guide wire being generally circular in cross-section having a diameter less than 0.018 inch, said guide wire being initially straight and having no stored energy within said guide wire prior to movement and bending of said guide wire, said guide wire being in a metallurgical state wherein said guide wire bends through small radius bends without buckling or kinking, thereby producing a high degree of tactile control, said guide wire having a low friction coating bonded thereto, said coating cured at a low temperature that is not detrimental to the straightness and strength of the nickel-titanium shape-memory alloy, said coating being less than 0.0015 inch in thickness to minimize the overall diameter of the guide wire, said coating generally extending along the length of said guide wire, said guide wire including a flexible wire fixed to and extending away from said far end of said guide wire beyond said coating, said uncoated flexible wire comprising a floppy tip for said guide wire.

10. A guide wire as in claim 9 wherein said shape-memory alloy is pseudo-elastic displaying reversible stress-induced martensite.

11. A guide wire as in claim 9 wherein said shape-memory alloy is super-elastic.

12. A guide wire as in claim 9 wherein at least a portion of said guide wire is non-uniform in cross-section exhibiting a stress-induced variable modulus at a point of bending of said portion due to high stress.

13. A guide wire as in claim 9 further including an inflatable balloon attached to the end of said guide wire and further including means to inflate said balloon.

14. A guide wire as in claim 9 wherein said flexible wire is helically wound and further including an additional safety wire interconnecting said guide wire and said flexible wire.

15. A guide wire as in claim 14 wherein said guide wire is gold-plated at the far end thereof, said flexible wire being connected to said guide wire in the area of said gold-plating by low temperature methods relative to welding, welding adversely affecting material properties.

* * * * *

UNITED STATES PATENT AND TRADEMARK OFFICE
CERTIFICATE OF CORRECTION

PATENT NO. : 5,120,308
DATED : June 9, 1992
INVENTOR(S) : Robert Hess

It is certified that error appears in the above-identified patent and that said Letters Patent is hereby corrected as shown below:

Column 1, line 62, after "alloys", insert a --.--;
Column 2, line 46, after "device", insert a --.--;
Column 7, line 28, after "super-elasticity", insert a --.--;
Column 8, line 32, after "friction", insert a --.--;
Column 8, line 39, after "wires", insert a --.--;
Column 9, line 29, after "balloon", insert a --.--;
Column 9, line 32, after "wire", insert a --.-- ;
Column 9, line 40, after "wire", insert --14--.

Signed and Sealed this

Fourteenth Day of September, 1993

Attest:

BRUCE LEHMAN

Attesting Officer

Commissioner of Patents and Trademarks